United States Patent [19]

Shirono et al.

[11] Patent Number: 5,730,995
[45] Date of Patent: Mar. 24, 1998

[54] ANTIBACTERIAL SUBSTANCE

[75] Inventors: Katsuhiro Shirono; Atsushi Tanaka; Kouichi Ohhama, all of Kitakyushu, Japan

[73] Assignee: Catalysts & Chemicals Industries Co., Ltd., Tokyo, Japan

[21] Appl. No.: 538,043

[22] Filed: Oct. 2, 1995

[30] Foreign Application Priority Data

Oct. 5, 1994 [JP] Japan ................. 6-264397

[51] Int. Cl.$^6$ .......................... A01N 25/06
[52] U.S. Cl. ............ 424/404; 424/65; 424/400; 424/401

[58] Field of Search .................. 424/65, 66, 67, 424/68, 400, 401, 404

[56] References Cited

U.S. PATENT DOCUMENTS 4,381,380  4/1983  Laveen et al. ............... 525/452
5,160,737  11/1992  Friedman et al. ............. 424/401

*Primary Examiner*—Shelley Dodson
*Attorney, Agent, or Firm*—Townsend & Banta

[57] ABSTRACT

An antibacterial substance, and more particularly, an antibacterial substance which displays antibacterial, anti-mold, and deodorizing effects when added to resins, paints, textile fibers and cosmetics.

12 Claims, No Drawings

ANTIBACTERIAL SUBSTANCE

BACKGROUND OF THE INVENTION

1. Field of the Invention

The present invention relates to an antibacterial substance, and more particularly to an antibacterial substance which shows antibacterial, anti-mold, and deodorizing effects when added in resin, paints, textile fiber and cosmetics.

2. Description of Related Art

There have been known antibacterial compositions in which a metallic component having antibacterial characteristics is carried on powder of such a substance as zeolite, silica-gel, and titanium oxide, such as those disclosed for instance, in Japanese Patent Laid Open Publication No. 225402/1990. However, the conventionally known antibacterial powdery compositions have the following problems:

(1) The dispersibility when added resin, paints, textile fiber, cosmetics or the like is poor, and also adhesiveness to resin moldings and textile fiber is low.

(2) The antibacterial characteristics does not develop effectively, and in order to obtain the desired antibacterial capability, it is necessary to add a quantity of antibacterial composition.

(3) When a large quantity of composition is added, aggregation of powder easily occurs, and also contents of metallic component increase, so that discoloration may occur in compositions in which an antibacterial component such as silver is used.

(4) When an antibacterial composition is mixed in raw resin for textile fiber for spinning, yarn is often cut if the composition is powdery and has a large particle size.

(5) In a case where paints containing powdery antibacterial composition are coated on a surface of a material such as resin to form a coating film for the purpose to add antibacterial characteristics thereto, the film thickness is apt to become large with lower film strength, and also separation easily occurs. Furthermore this type of technology can not be applied when transparency is required.

So inventors of the present invention proposed a novel antibacterial composition prepared by ion-exchanging metallic ions of inorganic oxo acid salt with other metal ions having antibacterial characteristics in Japanese Patent Application No.74088/1990 (Japanese Patent Laid-Open Publication No.275627/1991), but the effects were not satisfactory for solving the problems as described above.

Also Japanese Patent Laid-Open Publication No.258792/1989 discloses antibiotics containing alumina sol having antibacterial characteristics in which metal having antibacterial effect or a compound thereof is deposited on a surface of aluminium oxide in the alumina sol. It seems that the invention succeeded in solving, for instance, the problem (5) described above by making use a function of the alumina sol to form a coating film, but there sill remain the problems of transparency and (1) to (4) described above.

Furthermore Japanese Patent Laid-Open Publication No.321628/1992 proposes antibiotics comprising silver-colloidal particles having high antibacterial capability, but the colloid solution has grey-brown color with low transparency, and also silver component itself is colloidal particles, so that the substance easily aggregates and disadvantageously lacks stability.

SUMMARY OF THE INVENTION

It is an object of the present invention to provide novel antibacterial substance which can solve the problems specific antibacterial powdery compositions as described above and comprises a colloidal solution of inorganic oxide having antibacterial characteristics and excellent in transparency. Also it is another object of the present invention to provide antibiotics comprising a colloidal solution of antibacterial inorganic composition which are improved wetting characteristics to a surface of solid and are excellent in adhesiveness to resin moldings, textile fiber or the like.

The antibacterial substance according to the present invention is a colloidal solution of antibacterial inorganic oxide in which particles comprising an antibacterial metallic component and an inorganic oxide other than the antibacterial metallic component are dispersed, and the antibacterial substance is characterized in that the light transmittance at the wavelength of 500 nm in the colloidal solution having the solid-phase component concentration of 0.1 weight % is 50 % or more.

Also the antibacterial substance according to the present invention is a colloidal solution of antibacterial inorganic oxide in which particles comprising an antibacterial metallic component and an inorganic oxide other than said antibacterial metallic component are dispersed, and is characterized in that an average particle diameter of the particles is in a range from 3 to 500 nm, and at the same time a percentage of particles having a particle diameter in a range of the average particle diameter ±30% is 50% or more.

Also the antibacterial substance according to the present invention is a colloidal solution of antibacterial inorganic oxide in which particles comprising an antibacterial metallic component and an inorganic oxide other than the antibacterial metallic component are dispersed, and is characterized in that, assuming that weight of the antibacterial metallic component in the colloidal solution is A, and that weight of free antibacterial metallic component separated by means of ultracentrifugal separation of the colloidal solution is B, a value of bonding strength index (I) of the antibacterial metallic component expressed by B/A is $1.0 \times 10^{-2}$ or below.

The antibacterial substance according to the present invention should preferably include a surfactant as an additional ingredient.

DESCRIPTION OF THE PREFERRED EMBODIMENTS

The antibacterial substance according to the present invention is a colloidal solution in which fine particles (colloidal particles) comprising an antibacterial metallic component and an inorganic oxide other than the antibacterial metallic component are dispersed, and the antibacterial metallic component forms colloidal particles in a form of a mixture with an inorganic oxide or a compound, or is bonding to a surface of the colloidal particles of inorganic oxide. As the antibacterial metallic component, any of the generally known antibacterial metallic ingredient can be used, and for instance, silver, copper, zinc, tin, lead, bismuth, cadmium, chromium, and mercury are enumerated as the component available for the purpose. Especially one or more antibacterial metallic components selected from a group consisting of silver, copper and zinc is preferable from a view point of antibacterial effect, discoloration, and safety to human health.

A copper ion as the antibacterial component generates a color of blue, but a silver ion has no color. However, the silver ion changes to an aggregation or an oxide of metallic silver due to a photochemical reaction or an oxidation thereof, and also the color changes to brown or black. Especially to prevent discoloration of the silver component due to a photochemical reaction caused by ultraviolet ray, it is desirable to use titanium, zirconium, cerium, or zinc in combination with the silver component. This is because such a metal as titanium, zirconium, cerium, or zinc works as an ultraviolet ray absorbent and prevent discoloration of the silver component.

It is desirable that a quantity of an antibacterial metallic component in the antibacterial substance according to the present invention is in a range from 0.1 to 25 weight % when the solid-phase portion is converted to an oxide. If a quantity of the antibacterial metallic component is lower than 0.1 weight %, the antibacterial effect is not shown to its full extent. Also when a quantity of antibacterial metallic component is more than 25 weight %, there is no substantial difference from a case when the quantity is 25 weight %, and in a case of silver ingredient, if a rate of quantity increases, discoloration easily occurs. A preferable quantity of the antibacterial metallic component is in a range from 0.1 to 15 weight % when converted to an oxide.

On the other hand, as the inorganic oxide other than the antibacterial metallic component according to the present invention, inorganic oxides constituting generally known colloidal solutions can be enumerated. As the colloidal particles of inorganic oxide, colloidal particles of either single inorganic oxides or complex inorganic oxides can be used, and also a mixture thereof may be used.

Examples of the single inorganic oxides include $SiO_2$, $Al_2O_3$, $TiO_2$, $ZrO_2$, $Fe_2O_3$, $Sb_2O_5$, and $WO_3$. Examples of the complex inorganic oxides include oxides of combination of each of the oxides described above and other inorganic oxides such as $SiO_2$—$Al_2O_3$, $SiO_2$—$B_2O_3$, $SiO_2$—$P_2O_5$, $Al_2O_3$—$TiO_2$, $Al_2O_3$—$ZrO_2$, $Al_2O_3$—$B_2O_3$, $Al_2O_3$—$P_2O_5$, $TiO_2$—$CeO_2$, $TiO_2$—$ZrO_2$, $SiO_2$—$ZrO_2$, $SnO_2$—$Sb_2O_5$, $SiO_2$—$Al_2O_3$—$TiO_2$, $SiO_2$—$TiO_2$—$CeO_2$, $TiO_2$—$SiO_2$—$ZrO_2$, $SiO_2$—$Al_2O_3$—$MgO$, $SiO_2$-$Al_2O_3$—$CaO$, $SiO_2$—$TiO_2$—$Fe_2O_5$.

The antibacterial substance according to the present invention is characterized in that the light transmittance at the wavelength of 500 nm, when concentration of solid-phase material in the colloidal solution is 0.1 weight %, is 50% or more. Herein the light transmittance is defined as a relative value of transmittance of light having the wavelength of 500 nm in a colloidal solution of an antibacterial inorganic oxide in which concentration of solid-phase material is 0.1 weight %, said colloidal solution having a depth of 1 cm, assuming that transmittance of light having the wavelength of 500 nm in water having a depth of 1 cm is 100%.

If the light transmittance of a colloidal solution of an antibacterial inorganic oxide is less than 50%, when a paint prepared from the colloidal solution is applied onto a surface of resin moldings or the like, transparency of a coating film formed there is poor, so that such colloidal solution is not preferable. Especially in a case for the purpose to give antibacterial capability to textile fiber products, patterns or colors of the products are damaged, so that use of the coating for such purposes is not desirable. The light transmittance of the antibacterial substance according to the present invention should preferably be 60% or more, and more preferably in a range from 70 to 100%.

The antibacterial substance according to the present invention is characterized in that an average particle diameter of inorganic oxide particles constituting a colloidal solution is in a range from 3 to 500 nm, and at the same time that, as for distribution of the particle diameters, a percentage of particles having a diameter in a range of the average particle diameter ±30% is 50% or more.

In a case where an average particle diameter of the colloidal particles is 500 nm or more, generally transparency of a colloidal solution of antibacterial inorganic oxide is apt to become lower, and in a case where the average particle diameter is smaller than 3 nm, stability of the colloidal solution of antibacterial inorganic oxide is low, and the solution gels easily.

Furthermore in a case where a percentage of particles having a particle diameter in a range of the average particle diameters ±30% in the colloidal solution is 50% or less, the distribution of the particle diameter becomes broad, and transparency of the colloidal solution is apt to become lower. Also when a paint prepared from the colloidal solution is applied to a surface of a material such as resin to form a coating film, homogeneity of the film is poor, so that use of the coating for such purposes as described above is not desirable.

It is desirable that an average particle diameter of the colloidal particles is in a range from 5 to 250 nm. Also it is desired in relation to the distribution of particle diameter that a percentage of particles having a particle diameter in a range from the average particle diameter ±30% is 60% or more, and it is more preferable that the percentage is 70% or more.

The antibacterial substance according to the present invention is characterized in that, assuming that weight of an antibacterial metallic component in the colloidal solution is A and that of a free antibacterial metallic component separated by subjecting the colloidal solution to ultracentrifugal separation is B, a value of the binding strength index (I) of the antibacterial metallic component expressed by B/A is $1.0 \times 10 \times 10^{-3}$ or below.

The bonding strength index (I) is obtained as described below. Namely, weight (A) of metallic component in a colloidal solution of antibacterial inorganic oxide is measured with a plasma emission spectral analyzer by measuring a quantity of metallic atoms, and then a specified quantity of the colloidal solution of antibacterial inorganic oxide is separated for one hour with a ultracentrifugal separator rotating at 45,000 rpm to solid-phase materials and a solution, and a quantity of metallic atoms of antibacterial metallic components contained in the separated solution is measured to obtain weight (B) of the separated free antibacterial metallic component.

If the bonding strength index (I) is larger than $1.0 \times 10^{-3}$, a bonding strength of the antibacterial metallic component to the inorganic oxide colloidal particles is weak, so that the antibacterial metallic component easily elutes into a solvent of the colloidal solution. For this reason, when the fine particles are mixed in a painting composition and a coating film is formed with the mixture, durability of the antibacterial effect is rather poor, and also in a case where silver is used as an antibacterial metallic component, it may cause discoloration. The bonding strength index(I) of the antibacterial metallic component is preferably less than $5.0 \times 10^{-4}$, and more preferably less than $1.0 \times 10^{-4}$. In a case where two or more types of antibacterial metallic component are used, the bonding strength index(I) of each antibacterial metallic component should preferably be less than $1.0 \times 10^{-3}$.

Of the colloidal solutions of antibacterial inorganic oxide as described above, especially those in which fine particles comprise a complexe oxide comprising a antibacterial metallic component and an inorganic oxide other than the antibacterial metallic component have a small value of the bonding strength index (I) with a large value of the light transmittance as well as high antibacterial capability, so that the colloidal solutions are preferable.

A colloidal solution of antibacterial inorganic oxide in which fine particles of the complexe oxide as described above are dispersed can be prepared according to a method of producing a colloidal solution of complexe oxide as disclosed, for instance, in Japanese Patent Laid-Open Publication No. 132309/1993. In the method, alkaline metal, ammonium or silicate of organic base, an alkali soluble inorganic compound, and an aqueous solution containing an antibacterial metallic ingredient are simultaneously added in an alkali aqueous solution with pH of 10 or more to generate colloidal particles of inorganic oxide having formed a complexe oxide with the antibacterial metallic component.

Also the colloidal solution of antibacterial inorganic oxide can be prepared according to to the preparing method disclosed in Japanese Patent Laid-Open Publication No.270620/1988. Namely, in this method, an aqueous solution of titanic acid obtained by adding peroxide to gel or sol of titanic acid hydrate and an aqueous solution containing an antibacterial metallic component are heated under existence of silicon compound and/or zirconium compound or the like according to the necessity, and a colloidal solution in which particles of complexe inorganic oxide comprising an antibacterial metallic component and an inorganic oxide other than the antibacterial metallic component are dispersed is prepared.

Water as a dispersion medium in the colloidal solution of antibacterial inorganic oxide obtained according to the method described above can be substituted by such an organic solvent as methyl alcohol, ethyl alcohol, isopropyl alcohol, toluene, and methylethylketone to prepared a colloidal solution of antibacterial inorganic oxide containing an organic solvent as a dispersion medium.

Also concentration of the colloidal solution according to the present invention can be adjusted to that of a colloidal solution suited to normal use, but from a view point of stability of the colloidal solution, it is desirable to set the concentration as an oxide to a range from 1 to 30 weight %. Concentration of the colloidal solution can be adjusted to a desired concentration according to any of known methods using a ultrafiltration film.

Furthermore it is desirable in the antibacterial substance according to the present invention that a surfactant is additionally included in the colloidal solution of antibacterial inorganic oxide described above. Any type of surfactant can be used for that purpose on the conditions that the surfactant will not give severe damages to stability of the colloidal solution, and for instance in a case where a dispersion medium for the colloidal solution is water, anion-based surfactant or amphoteric surfactant is preferable.

The anion-based surfactants include various types of soap such as oleic acid potassium soap, fatty acid soda soap, alkylbenzen sodium sulfonate, dodecyl sodium sulfate, dialkylsulfo sodium succinate, alkylnaphthalene sodium sulfonate, alkyl naphthalene sodium disulfonate, polyoxyethylene laurylether sodium sulfate, lauryl ammonium sulfate, alkyl potassium phosphate, polyoxyethylene alkyl phosphate ester, polycarboxylic acid, and β-naphthalene sulfonic acid formalin-condensated product.

The amphoteric surfactants include amino-acid derivatives of N-alkyl-N,N-dimethylammoniumbetain, polyoxyethylene alkylamine, polyoxyethylene laurylether, polyoxyethylene oleylether, polyoxyethylene nonylphenylether, polyoxyethylene higher alcohol ether, sorbitan monostearate, sorbitan monolaurate, and polyoxyethylene sorbitan monolaurate.

A quantity of surfactant contained in the antibacterial substance is preferably in a range from 0.001 to 1.0 weight %. If content of surfactant in the antibacterial substance is less than 0.001 weight %, an effect of addition of surfactant as described later is not obtained, and if the content is more than 1.0 weight %, the effect of addition does not change dramatically, so that it is not economical.

When antibacterial substance comprising a colloidal solution of antibacterial inorganic oxide containing surfactant is contacted to such as a material as resin moldings or textile fiber, wetting characteristics of a surface of the material is improved, and the dispersibility or adhesiveness is substantially improved. Improvement in dispersibility or adhesiveness of antibacterial substance is effective especially to hydrophobic materials.

In a case of the antibacterial substance containing surfactant according to the present invention, the surface tension should preferably be less than 45 dyne/cm, and more preferably be less than 40 dyne/cm. If the surface tension is higher than 45 dyne/cm, the effect to improve the wetting characteristics of the materials described above becomes smaller.

The antibacterial substance according to the present invention can be used for a variety of applications as described below.

(1) Application to textile fiber

The antibacterial substance according to the present invention can give antibacterial, anti-mold, and deodorizing characteristics to various types of textile fiber. As the textile fiber as an object for this application, the following types of textile fiber can be enumerated: natural textile fiber (such as cotton, wool, silk, jute, pulp), semi-synthetic textile fiber (such as rayon, cupro, and acetate), and synthetic textile fiber (such as polyester, polyurethane, polyvinyl acetel, polyamide, polyolefin, polyvinyl chloride, polyvinilidene chloride, polyacrylnitryl, polyfluorine). Any of known methods such as contacting the antibacterial substance according to the present invention to the textile fiber and then washing with water and drying, or spraying the antibacterial substance according to the present invention over the textile fiber is available for giving the antibacterial capability to these types of textile fiber.

Textile fiber as an object for giving the antibacterial capability includes raw textile fiber, intermediate textile fiber products, and final textile fiber products. The final textile fiber products include, for instance, general articles of clothing (such as blouse, skirt, trousers, dresses, sweaters, cardigans, aprons, uniforms, pants, stockings, socks, pantystockings, brassieres, girdles, accessaries to Japanese clothes, 'tabi', padding cloth, padding cloth for 'Obi'), accessaries (such as handkerchiefs, scarves, hats, gloves, watch belts, bags, hand bags, shoes, footwears, and matting for shoes), interior products (such as curtains, blinds, carpets, mats, table clothes, toiletaries, and car sheet covers), miscellaneous goods for daily use (such as towels, table napkins, mops, tents, sleeping bags, stuffed dolls, filters, and brushes), bedding (such as brackets, bed sheets, towelkets, bed covers, bed side clothes, and internal cotton), products used in hospitals (white clothes worn by nurses, clothes for surgery operations, masks, dumpers, and dumper covers), and fishing tools (such as ropes and fishing nets).

The antibacterial substance, especially antibacterial substance containing a surfactant according to the present invention is well assimilated to textile fiber, so that the antibacterial capability can easily be given to the final textile fiber products as described above by washing them and then adding the antibacterial substance during rinsing.

(2) Application to resins and rubbers

The antibacterial substance according to the present invention can give antibacterial, anti-mold, and deodorizing capabilities to thermoplastic resins or thermosetting resins.

Types of resin available for this application include, for instance, phenolic resin, urea resin, melamine resin, alkyd resin, diaryl phthalate resin, epoxy resin, polyurethane resin, thermosetting resins such as silicon resin, polyvinyl chloride resin, polychloride vinyliden resin, fluoride resin, polyvinyl fluoride resin, polyvinylidene fluoride resin, polyvinyl acetate, polyvinyl alcohol resin, polyvinyl formalic resin, saturated polyester resin, polyethylene resin, polypropylene resin, polystyrene resin, ABS resin, acrylic resin, polyamide resin, polyacetal resin, polyether chloride resin, polycarbonate resin, polyscrylate resin, ethyl cellulose, cellulose acetate, and cellulose nitrate. Also types of rubber available for this purpose include elastomers or rubbers such as natural rubber, isoprene rubber, acrylnitryl rubber, acryl rubber, butadiene rubber, butyl rubber, styrene rubber, chloroprene rubber, chlorohydrin rubber, polyolefin rubber, urethane rubber, polysulfide rubber, silicon rubber, fluorine rubber, and fhorosilicon rubber.

To give the antibacterial capability to the resins or rubbers, known methods can be employed including a method in which the antibacterial substance according to the present invention is added to the raw material and an antibacterial resin or an antibacterial rubber is obtained, a method in which the antibacterial substance is added to a resin for master batch, a method in which the antibacterial substance is contacted to resin moldings under raised temperature, or a method in which the antibacterial substance is applied onto resin moldings.

The resin moldings available for this purpose includes plates, robs, pipes, tubes, films, sheets, vessels, foams, and other various types of moldings or composite moldings. As concrete materials of the resin moldings available for this purpose, the following items can be enumerated; interior equipment (such as floor materials, wall materials, lavatory seats, bath tubs, washstands, sculleries, tables), kitchen tools (such as cups, glasses, chop-sticks, spoons, lunch boxes, trays, tableware made from resin such as water bottles, cooking plates, vessels for drink, and vessels within a refrigerators), accessaries (such as combs, shaving tools, brushes, earphones, frames of looking-glass), items for nursing (such as tools, nursing bottles, teething rings), miscellaneous items for daily use (such as buckets, hoses, dustbins, dustpans, and general vessels), packing materials (such as dust bugs, and packing films), interior items for cars (such as handles and sheets), items touched by many and unspecified persons (straps and grips thereof for vehicles, chairs and benches in waiting rooms, handrails, various types of pushbutton, switches, receptacles, cocks for faucet, telephone receivers, and 'pachinko' machine), articles for medical use (tableware used in hospitals, injectors, stethoscopes, gloves for operation, intravenous feeding bottles, catheter, resin parts of medical equipment), stationeries and musical instruments (such as ball-point pens, pencils, scales, CD disks, record disks, and video tapes), electronic equipment (such as refrigerators, dishwashers, electronic washing machine, cleaners, air conditioners, television sets, and electronic computers including personal computers).

(3) Application to paints

It is possible to give antibacterial, anti-mold, and deodorizing capabilities to various types of coating (coating compositions). The antibacterial coating comprises an antibacterial substance, a film-forming agent, and a solvent, if necessary, and types of antibacterial coating include an oil coating, a alcohol coating, cellulose coating, synthetic resin coating, aqueous coating, and rubber coating. The antibacterial painting is prepared by adding the antibacterial substance to the film-forming agent or solvent, or by adding the antibacterial substance to or mixing the antibacterial substance in raw materials in a production process of other composition or in any process of forming a coating film. As the film-forming agent, generally such materials as natural resin, rubber, or synthetic resins are used, while as a solvent, usually water, botanic oil, alcohols, petroleums, esters, and ketones are used.

(4) Applications in other fields

With the antibacterial substance according to the present invention, it is possible to give the antibacterial, anti-mold, and deodorizing capabilities to such materials as construction materials for houses, materials for fixtures (such as wall paper, 'husuma', 'shoji', and 'tatami'), ceramics (such as tile, ceramics, and porcelains), leather products (such as bugs, shoes, leathers, or purses), wood products (such as desks, shelves, chests of drawers, floor plates, ceiling plates, and interior finishes), paper products (such as tissue paper, linerboard, paper pups, and paper dishes), glass products (such as vases, and water products), metallic products (sash, kettles, and air conditioners for cars).

Also the antibacterial substance according to the present invention can be used in water cleaners, water-processing agents for water in swimming pool, materials for cosmetics, life-prolonging agents for flowers, materials for prevention of diseases of plants, anti-algae agents, rust preventives, deodorants for sand beds as cat's lavatory or the like, preventives for ringworm, or in printing inks, various types of filter, and seedbeds for such plants as orchid.

Detailed description is made hereinafter with reference to related experiments, but it should be noted that these experiments are introduced only as examples. The present invention should not be limited in scope to the results of these experiments. The scope of the present invention is defined by claims. Also, any alteration or change constituting an equivalent claim shall be regarded as within the scope of the present invention.

Example 1

[Preparation of a colloidal solution of an antibacterial inorganic oxide]

Titanium sulfide is dissolved in pure water, and an aqueous solution containing $TiO_2$ by 1.0 weight % was obtained. Agitating this aqueous solution, 28 weight % ammonia water was gradually added, and white slurry was obtained. This slurry was filtered and washed, and a cake of titanic acid hydrate was obtained. 31.4 g of this cake was diluted by adding pure water so that density of the aqueous water will be 1.0 weight %, and then 219.8 g of 33 weight % hydrogen peroxide was added, the mixture was heated for 14 hours under 80° C. to pyrolyze the hydrogen peroxide, and 3136 g of 1.0 weight % aqueous solution as $TiO_2$ was obtained. This titanic acid solution was transparent but had a color of yellow brown, and the pH was 8.2.

Then an aqueous solution containing ammine complex salt of silver was prepared by dissolving 0.64 g of silver oxide in a mixture solution of 20 g of 28 weight % ammonia water and 350 g of pure water, and after 38.7 g of 20 weight % silica sol was added in the aqueous solution, an aqueous solution obtained by dissolving 15.4 g of zirconium ammonium carbonate in 170 g of pure water was added to the mixture solution. The aqueous solution of this mixture was added to the titanic acid solution described above, and the mixture was heated for 24 hours under the temperature of 150° C. to generate colloidal particles, and then the colloidal particles were filtered by a ultrafiltration film and the the colloidal solution of composite oxide containing silver ingredient as the oxide by 1.3 weight % was obtained.

The pH of this colloidal solution was 7.5, and a concentration of the solid phase ingredients was 1.0 weight %. The average particle diameter of the colloidal particles were 24.3 nm, and the percentage of particles having diameter in a range of the average particle diameter ±30% was 72%. Also the value of the bonding strength index (I) of the silver ingredient in the colloidal solution was $0.6 \times 10^{-4}$.

The transmittance of light having a wavelength of 500 nm, when the concentration of solid phase ingredients of the colloidal solution was 0.1 weight %, was measured with a spectrophotometer (produced by Hitachi Corp.: U-2000), and the transmittance was 79.9%.

The surface tension of this colloidal solution was 50.3 dyne/cm. The surface tension was measured with an automatic surface tension balance (manufactured by Kyowa Kaimen Kagaku Corp.; CBVP-A3) under the solution temperature of 25° C. It should be noted that generation of precipitates was not observed after the colloidal solution was left for 3 months.

Example 2

0.2 g of surfactant (produced by Kao Corp.: T-P) was added to 100 g of a colloidal solution of antibacterial inorganic oxide obtained in Example 1 in which the concentration of solid phase ingredients was 1.0 weight %, the mixture was fully agitated, and s colloidal solution of antibacterial inorganic oxide containing a surfactant was obtained.

The diameters of colloidal particles, the distribution of particle diameters, the value of bonding strength index (I) of silver component, and the transmittance of the colloidal solution was not different from those of the colloidal solution according to Example 1, but the surface tension was 22.3 dyne/cm, lower as compared to that in Example 1. The colloidal solution was as stable as that in Example 1.

Example 3

25 kg of silica sol containing silica by 5 weight % (supplied from Catalysts & Chemicals Industries Co., Ltd., SI-200P, particle diameter:200 nm) was used as seed, and pH of the silica sol was adjusted by adding alkali water to 12.5, and then the sol was agitated for 30 minutes under the temperature of 95° C. 37.5 kg of 0.5 weight % sodium aluminate and 37.5 kg of 1.5 weight % water glass were added in the seed solution at a rate of 78.1 g/minute over a period of 8 hours respectively, and aged for one hour under the temperature of 95° C. Then the solution was cooled to the room temperature, and washed in 100 times of distilled water using a ultrafiltration film, and silica alumina sol containing solid phase ingredients by 1.0 weight % was obtained. 50 kg of this sol was heated to 40° C., and an aqueous solution of silver nitrate obtained by dissolving 4.13 g of silver nitrate in 10 liters of distilled water was added at a rate of 55.5 g/minute for 3 hours, and anion exchange resin was added to the sol so that pH of the sol was maintained at 8.0. Then said sol was washed in 100 times of distilled water using a ultrafiltration film, and the colloidal solution of composite oxide containing silver component as oxide by 1.3 weight % was obtained.

The pH of the colloidal solution was 8.5, and the concentration of solid phase ingredients was 1.0 weight %. The average particle diameter of the colloidal particles in this colloidal solution was 210 nm, and the percentage of particles having diameter in a range of the average particle diameter ±30% was 76%. The value of bonding strength index (I) of the silver component in the colloidal solution was $0.9 \times 10^{-4}$.

The transmittance of light having the wavelength of 500 nm, when the concentration of solid phase ingredients in this colloidal solution was 0.1 weight %, was measured by the spectrophotometer described above, and the transmittance was 76.1%.

The surface tension of this colloidal solution was 54.1 dyne/cm, and generation of precipitates was not observed after the colloidal solution was left for 3 months.

Example 4

0.2 g of surfactant (produced by Kao Corp.: T-P) was added to 100 g of a colloidal solution of antibacterial inorganic oxide obtained in Example 3 in which the concentration of solid phase ingredients was 1.0 weight %, the mixture was fully agitated, and a colloidal solution of antibacterial inorganic oxide containing a surfactant was obtained.

The diameters of colloidal particles, the distribution of particle diameters, the value of bonding strength index (I) of the silver component, and the transmittance of the colloidal solution was not different from those of the colloidal solution according to Example 3, but the surface tension was 25.2 dyne/cm, lower as compared to that in Example 3. The colloidal solution was as stable as that in Example 3.

Example 5

An aqueous solution containing ammine complex salt of silver and silica sol were added to a titanic acid solution in the same manner as described in Example 1, and the mixture was heated for 8 hours under the temperature of 110° C. to generate colloidal particles, and then the colloidal particles were filtered by a ultrafiltration film and the the colloidal solution of composite oxide containing silver component as the oxide by 1.3 weight % was obtained.

The pH of this colloidal solution was 7.9, and the concentration of the solid phase ingredients was 1.0 weight %. The average particle diameter of the colloidal particles were 8.8 nm, and the percentage of particles having diameter in a range of the average particle diameter ±30% was 73%. Also the value of the bonding strength index (I) of the silver component in the colloidal solution was $0.4 \times 10^{-4}$.

The transmittance of light having a wavelength of 500 nm, when the concentration of solid phase ingredients of the colloidal solution was 0.1 weight %, was measured with by the spectrophotometer described above, and the transmittance was 85.0%.

The surface tension of this colloidal solution was 50.1 dyne/cm, and generation of precipitates was not observed after the colloidal solution was left for 3 months.

Example for Comparison 1

1000 cc of alumina sol with a density of 10 weight % (supplied from Nissan Kagaku Corp.: Alumina Sol-200) and 10 g of silver carbonate (supplied from Wako Junyaku Corp.) were put in an automatic mortar to grind the silver carbonate, and the ground silver carbonate was forcefully applied to the surface of alumina. This sol was diluted with pure water by 10 times, and a colloidal solution containing solid-phase ingredients by 1.0 weight % was obtained.

The average particle diameter of the colloidal particles in the colloidal solution was 100 nm, and the percentage of particles having diameter in a range of the average particle diameter ±30% was 48%.

Also the value of bonding strength index(I) of the silver component of the colloidal solution was $7.3\times10^{-2}$, and the color of the solution was started changing to black in several hours.

The transmittance of light having the wavelength of 500 nm, when the concentration of solid-phase ingredients in this colloidal solution was 0.1 weight %, was measured with the spectrophotometer described above, and the light transmittance was 49%.

Example 6

[Testing for evaluating the antibacterial capability]

Testing for evaluating the antibacterial capability of samples prepared according to the method described below was conducted using the antibacterial substances obtained in Example 1-5 and Example for Comparison 1. Results of testing are shown in Table 1-6.

100 g of each of the antibacterial substances obtained in Example 1-5 and Example for Comparison 1 (each containing solid-phase ingredients by 1 weight %) was heated to 50° C., and 30 g of cotton cloth, 30 g of polyester cloth, 10 g of Japanese paper, an ABS resin plate (100×100×3 mm) and PVC floor materials (100×100×3 mm) were steeped into each sample for 10 minutes respectively. Then the samples of cloth and Japanese paper were dried for 10 minutes under the temperature of 130° C., and the samples of resin plate and floor materials were dried for 10 minutes under the temperature of 60° C. to obtain samples for the testing.

Also 3 g of each of the antibacterial substances obtained in Example 1-5 and Example for Comparison 1 above was added to 100 g of water-soluble acrylic resin (supplied from Nippon Jun'yaku Corp., Julimer-FC65) so that the concentration would be 3 weight % respectively, and the mixture solution was well agitated. The antibacterial resins were applied onto an aluminium plate for form a coating film having a thickness of 3 μm, and was dried for 30 minutes under the temperature of 60° C., (1) Testing for antibacterial capability B-coli and yellow spaphylococcus were suspended in physiological brine, 30 μl of the mixture was dripped onto the surface of each sample cut into a piece having a size of 30×30 mm respectively, the samples were left for 24 hours under the temperature of 28° C., a number of living bacteria was counted, and the killing rate (R) was obtained from the following equation:

$$R(\%)=100\times(N_0-N)/N_0$$

In the above equation, $N_0$ is a number of initial living bacteria, and N is a number of living bacterial in 24 hours.

(2) Testing for antiweatherability

Testing for antiweatherability was performed for 100 hours using a weather meter (supplied from Gas Shiken Kiki Corp.), and discoloration of each sample was observed.

○: not observed discoloration
Δ: observed slight discoloration
X: observed discoloration (3) Testing for discoloration A part of each sample was dried by sunlight, and free silver ion was reduced to metallic silver due to ultraviolet ray. The discoloration to brown or black of each sample was observed.

○: not observed discoloration
Δ: observed slight discoloration
X: observed discoloration

TABLE 1

[Example 1]

| Samples | Killing Rate (%) | | Antiweather-ability | Discoloration |
|---|---|---|---|---|
| | B-coli | Spaphylococcus | | |
| Cotton cloth | 100 | 100 | ○ | ○ |
| Polyester cloth | 98.9 | 99.5 | ○ | ○ |
| Japanese paper | 100 | 100 | ○ | ○ |
| ABS resin plate | 99.6 | 100 | ○ | ○ |
| Floor materials | 100 | 100 | ○ | ○ |
| Aluminium plate | 100 | 100 | ○ | ○ |

TABLE 2

[Example 2]

| Samples | Killing Rate (%) | | Antiweather-ability | Discoloration |
|---|---|---|---|---|
| | B-coli | Spaphylococcus | | |
| Cotton cloth | 100 | 100 | ○ | ○ |
| Polyester cloth | 99.6 | 100 | ○ | ○ |
| Japanese paper | 100 | 100 | ○ | ○ |
| ABS resin plate | 100 | 100 | ○ | ○ |
| Floor materials | 100 | 100 | ○ | ○ |
| Aluminium plate | 100 | 100 | ○ | ○ |

TABLE 3

[Example 3]

| Samples | Killing Rate (%) | | Antiweather-ability | Discoloration |
|---|---|---|---|---|
| | B-coli | Spaphylococcus | | |
| Cotton cloth | 95.3 | 96.9 | ○ | ○ |
| Polyester cloth | 89.8 | 90.9 | ○ | ○ |
| Japanese paper | 100 | 100 | ○ | ○ |
| ABS resin plate | 86.1 | 86.2 | ○ | ○ |
| Floor materials | 91.0 | 93.5 | ○ | ○ |
| Aluminium plate | 100 | 100 | ○ | ○ |

TABLE 4

[Example 4]

| Samples | Killing Rate (%) | | Antiweather-ability | Discoloration |
|---|---|---|---|---|
| | B-coli | Spaphylococcus | | |
| Cotton cloth | 96.3 | 97.0 | ○ | ○ |
| Polyester cloth | 91.2 | 93.0 | ○ | ○ |
| Japanese paper | 100 | 100 | ○ | ○ |
| ABS resin plate | 90.8 | 91.4 | ○ | ○ |
| Floor materials | 93.5 | 95.5 | ○ | ○ |
| Aluminium plate | 100 | 100 | ○ | ○ |

TABLE 5

[Example 5]

Killing Rate (%)

| Samples | B-coli | Spaphylo-coccus | Antiweather-ability | Discolo-ration |
|---|---|---|---|---|
| Cotton cloth | 100 | 100 | ○ | ○ |
| Polyester cloth | 100 | 100 | ○ | ○ |
| Japanese paper | 100 | 100 | ○ | ○ |
| ABS resin plate | 100 | 100 | ○ | ○ |
| Floor materials | 100 | 100 | ○ | ○ |
| Aluminium plate | 93.1 | 95.9 | ○ | ○ |

TABLE 6

[Ex. for Comp. 1]

Killing Rate (%)

| Samples | B-coli | Spaphylo-coccus | Antiweather-ability | Discolo-ration |
|---|---|---|---|---|
| Cotton cloth | 55.1 | 58.0 | X | X |
| Polyester cloth | 49.2 | 51.3 | X | X |
| Japanese paper | 85.3 | 86.2 | Δ | X |
| ABS resin plate | 61.1 | 59.9 | Δ | Δ |
| Floor materials | 64.1 | 66.6 | Δ | Δ |
| Aluminium plate | 89.1 | 90.3 | X | X |

What is claimed is:

1. An antibacterial substance which is a colloidal solution of antibacterial inorganic oxide with particles comprising an antibacterial metallic component and an inorganic oxide other than said antibacterial metallic component dispersed therein, wherein transmittance of light having a wavelength of 500 nm is from 50–100% when a concentration of solid-phase ingredients is 0.1 weight %.

2. The antibacterial substance according to claim 1, wherein said transmittance is from 60–100%.

3. The antibacterial substance according to claim 1, wherein said colloidal solution furthermore contains a surfactant.

4. The antibacterial substance according to claim 3, wherein said surfactant is contained in a range from 0.001 to 1.0 weight %.

5. An antibacterial substance which is a colloidal solution of antibacterial inorganic oxide with particles comprising an antibacterial metallic component and an inorganic oxide other than said antibacterial metallic component dispersed therein, wherein an average particle diameter of the particles is in a range from 3 to 500 nm and a percentage of particles having a diameter in a range of the average particle diameter ±30% is from 50–100%.

6. The antibacterial substance according to claim 5, wherein a percentage of particles having a diameter in a range of the average particle diameters ±30% is from 60–100%.

7. The antibacterial substance according to claim 5, wherein said colloidal solution furthermore contains a surfactant.

8. The antibacterial substance according to claim 7, wherein said surfactant is contained in a range from 0.001 to 1.0 weight %.

9. An antibacterial substance which is a colloidal solution of antibacterial inorganic oxide with particles comprising an antibacterial metallic component and an inorganic oxide other than said antibacterial metallic component dispersed therein, wherein, assuming that weight of an antibacterial metallic component in said colloidal solution is A and weight of the free antibacterial metallic component by subjecting said colloidal solution to ultracentrifugal separation processing is B, a value of the bonding strength index (I) of the antibacterial metallic component expressed by B/A is in a range from 0.0 to $1.0 \times 10^{-3}$.

10. The antibacterial substance according to claim 9, wherein a value of said bonding strength index (I) is in a range from 0.0 to $5.0 \times 10^{-4}$.

11. The antibacterial substance according to claim 9, wherein said colloidal solution furthermore contains a surfactant.

12. The antibacterial substance according to claim 11, wherein said surfactant is contained in a range from 0.001 to 1.0 weight %.

* * * * *